United States Patent [19]

Brown et al.

[11] Patent Number: 5,110,557
[45] Date of Patent: May 5, 1992

[54] BLOOD SAMPLE COLLECTION APPARATUS

[76] Inventors: Bradley V. Brown, 11573 Monrovia St., Overland Park, Kans. 66210; Rodney Laible, R.R. 1, Box 37, Bennington, Nebr. 68007

[21] Appl. No.: 549,953

[22] Filed: Jul. 9, 1990

[51] Int. Cl.$^5$ .............................................. B01L 11/00
[52] U.S. Cl. ................................... 422/101; 128/637; 128/763; 128/765; 128/766; 604/76
[58] Field of Search ..................... 422/101; 73/864.01, 73/863.23; 128/637, 760, 763, 765, 766; 604/76

[56] References Cited

U.S. PATENT DOCUMENTS 3,113,688 12/1963 Campbell ........................ 73/864.03
4,507,955 4/1985 Haase ............................. 73/864.01

Primary Examiner—Robert J. Warden
Assistant Examiner—Laura E. Collins
Attorney, Agent, or Firm—John A. Beehner

[57] ABSTRACT

A blood sample collection apparatus includes a removable plug adapted to fit within the open end of a blood collection tube. A vacuum tube extends through the plug for evacuating air from the collection tube. A pickup tube protrudes outwardly from the plug for supplying blood to a drop tube extending downwardly from the plug with its lower end positioned within the collection tubes based substantially below the lower end of the vacuum tube. A first filter on the plug is operatively interposed between the lower end of the vacuum tube and the air within the air collection tube for filtering the air drawn through the vacuum tube. A portable hand-held vacuum source is adapted for connection to the vacuum tube for applying a vacuum to the collection tube. The first filter has an exterior surface engaged against the interior periphery of the collection tube, which exterior surface has a plurality of grooves formed therein for filtering air through the grooves between the filter and interior periphery of the collection tube.

9 Claims, 2 Drawing Sheets

BLOOD SAMPLE COLLECTION APPARATUS

BACKGROUND OF THE INVENTION

The present invention is directed generally to a blood sample collection apparatus capable of quickly and easily collecting sufficient blood from a puncture site on a patient for testing of the blood and more particularly to such an apparatus which protects the medical attendant from contamination and which assures a high quality blood sample.

Various devices and methods have been used in the past for collecting blood from a puncture site on a patient's finger, ear, heel or other body part. A common apparatus is a small capillary tube which fills with blood by capillary action. These tubes are so small, however, that one cannot collect a sufficient quantity of blood for common blood tests so five or six are generally needed.

Another device for collecting blood samples is a collection tube having a scoop formed on the open end thereof to scoop the blood off of a finger. There are two problems with the use of this device. First, it's messy. Blood often runs down the patient's finger and even on the hands of the medical attendant as well, creating exposure to A.I.D.S. and like diseases. Secondly, the sample may be contaminated with tissue fluids from squeezing of the finger. Compression of the finger can cause hemolysis and the release of hemoglobin which can alter blood test results.

Finally, Campbell, U.S. Pat. No. 3,113,688, discloses a blood collector wherein a collection tube is closed with a plug having a hose extended therefrom for evacuating the tube by the medical attendant sucking on the free-end of the hose. Blood collected from a puncture site is deposited into the tube on the underside of the plug adjacent the open end of the tube communicating with the suction hose, such that at least portions of the blood sample may be easily sucked into the medical attendant's mouth. Devices which operate by suction from the mouth of the operator are believed to be prohibited by federal regulations. Guidelines promulgated by the Center for Disease Control on Atlanta, Georgia, likewise advise against the use of such devices.

Accordingly, a primary object of the invention is to provide an improved blood sample collection apparatus.

Another object to provide such an apparatus wherein collected blood is deposited into a collection tube near the bottom of the tube in substantial spaced relation below the opening through which a vacuum is applied to the tube to prevent blood from being drawn into the vacuum tube and to the pump.

Another object is to provide such an apparatus wherein blood is deposited adjacent the anticoagulant in the bottom of the tube to bubble the blood to effect mixing with the anticoagulant and prevent clotting.

Another object is to provide a blood sample collection apparatus which may be conveniently held at any desired angle for collecting blood without danger of the blood being drawn into the vacuum source.

Another object is to provide such an apparatus with a filter to block the flow of blood to the vacuum source.

Another object is to provide such an apparatus with a simple yet effective filter that operates regardless of the angle at which the tube is held and regardless of the extent to which the tube is filled within the capacity of the tube.

Another object is to provide such an apparatus including a hand-held reusable vacuum source which may be conveniently and comfortably held in either hand and readily connected to and disconnected from a blood collection tube.

Another object is to provide a blood sample collection apparatus including a disposable plug for use in filling each collection tube.

Another object is to provide such an apparatus wherein the vacuum source includes an electric vacuum pump and a second filter to prevent air born viruses from being spread to the ambient air.

Finally, an object of the invention is to provide a blood sample collection apparatus which is simple and rugged in construction, economical to manufacture and efficient in operation.

SUMMARY OF THE INVENTION

The blood sample collection apparatus of the invention includes a blood collection tube having open and closed ends and a plug adapted to fit within and seal the open end. A vacuum tube extends through the plug for evacuating air from the collection tube. Likewise, a pickup tube protrudes outwardly from the plug for drawing blood from a puncture site. The pickup tube communicates with a drop tube extending downwardly from the plug and having a lower end positioned within the blood collection tube and spaced substantially below the lower end of the vacuum tube. A first filter associated with the plug is operatively interposed between the lower end of the vacuum tube and the air within the blood collection tube for filtering the air drawn through the vacuum tube to prevent blood from being drawn into the vacuum. Finally, a portable hand-held vacuum source is provided for connection to the vacuum tube.

The first filter is preferably a ring having an exterior surface adapted to engage the interior periphery of the blood collection tube. The exterior surface has a plurality of grooves formed therein for filtering air directed through those grooves between the ring and the collection tube. A second filter is preferably provided on the hand-held vacuum source to prevent the spread of air born viruses to the ambient air and as a final screen to keep blood from the vacuum source.

The provision of a hand-held powered vacuum source enables the use of an evacuated tube for collecting blood samples without the danger of exposure of the operator to diseases, as in the case of a hose adapted for suction by mouth. The long drop tube insures that the blood sample will be deposited near the base of the tube where it is least likely to be aspirated into the vacuum source. Furthermore, the long drop tube is operative regardless of the angle at which the collection tube is disposed and furthermore, deposits the blood sample adjacent the anticoagulant to prevent clotting and to assure the high quality of the collected sample. The plug and associated main filter are economically manufactured and are intended to be disposed of after each sanitary single patient usage. The collection tube includes an integral hinged cap operative to close the open end of the tube to prevent spillage of the sample in the centrifuge and while handling and to further minimize air contact with the blood.

DESCRIPTION OF THE PREFERRED EMBODIMENT

Figure 1:
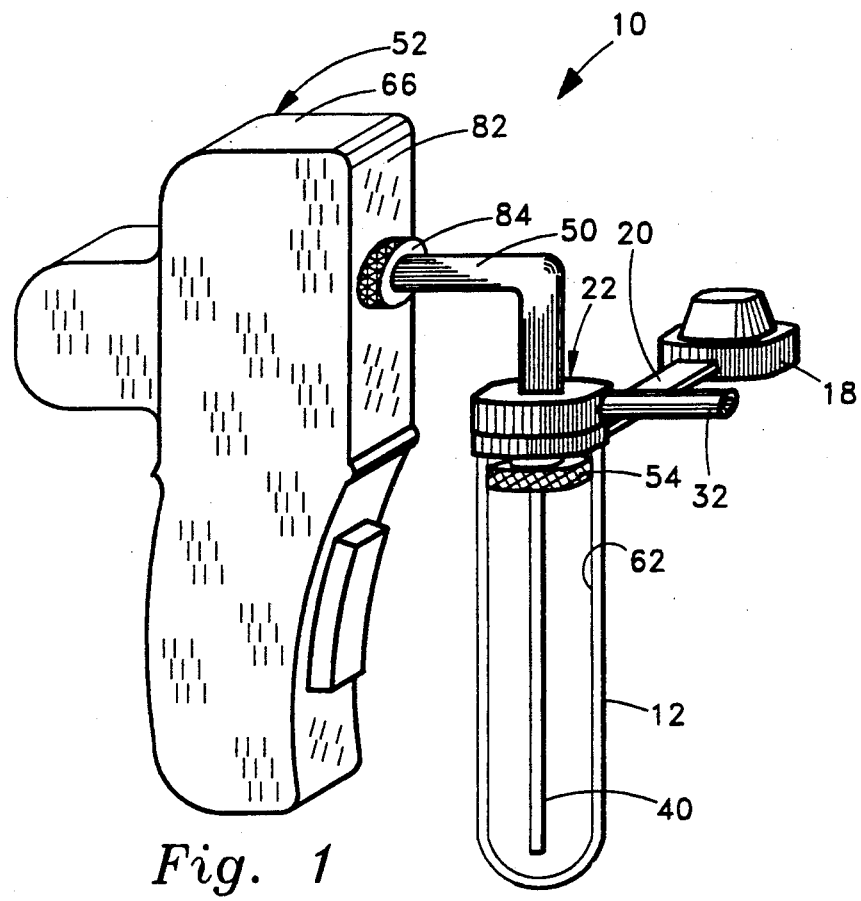
FIG. 1 is a perspective view of the blood sample collection apparatus of the invention.

The blood sample collection apparatus 10 of the present invention is illustrated in the drawings as including a blood collection tube 12 having an open end 14 and closed end 16 similar to a conventional test tube but with an integral closure Cap 18 connected to the tube by a flexible hinge strap 20 for closing the tube once a sample has been collected. Tube 12 is preferably a 750 microliter tube. Accordingly, a sample which fills between one third and one half of the tube affords sufficient blood for the 250 to 550 microliters required for common tests.

A removable plug 22 fits within and seals the open end 14 of the blood collection tube 12. The plug has a stepped rod shape including a central plug portion 24, and increased diameter top stopper portion 26 which engages the open end of the collection tube 12 to limit the penetration of the plug portion, and a bottom spacer portion 28 extending into the tube and defining an annular chamber 30 around it. The plug is preferably formed of a resilient rubber-like plastic material to effectively plug the open end of collection tube 12.

Figure 4:
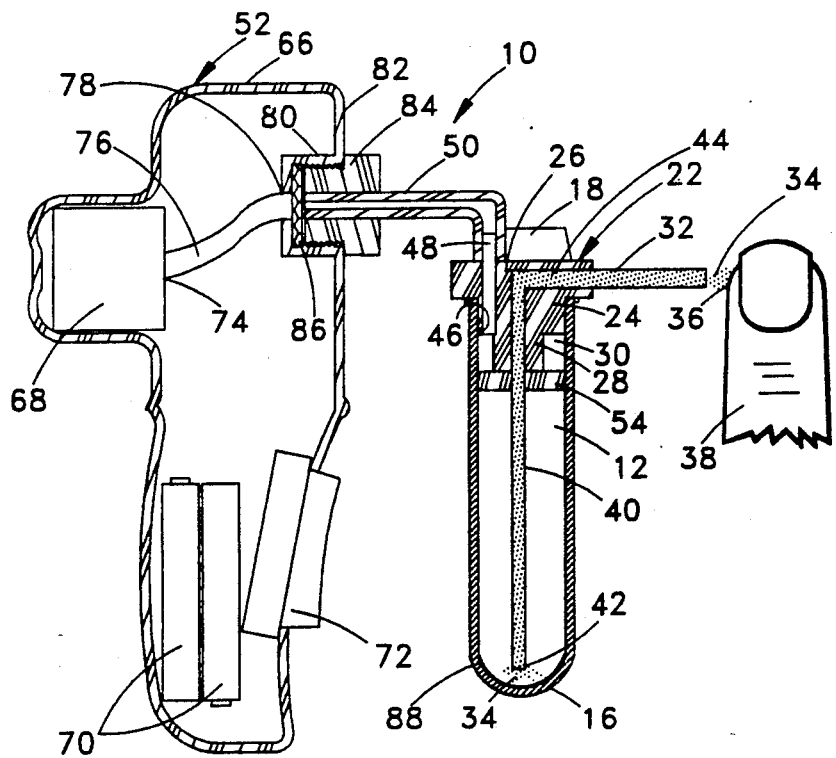
FIG. 4 is a side sectional view of the invention in use.

Referring to FIG. 4, a pickup tube 32 protrudes outwardly from stopper portion 26 for drawing blood 34 from a puncture site 36 on a patient's finger 38, earlobe, or other body part. A drop tube 40 extends downwardly through plug spacer portion 28 and has a lower end 42 positioned within the collection tube 12 at a position spaced substantially below the bottom of plug portion 24 through which an opening is provided to the vacuum source as described below. A conduit 44 is provided within plug 22 for connecting the pickup tube 32 and drop tube 40 so that blood drawn into the pickup tube is deposited into the blood collection tube 12 through the lower end of the drop tube 40. Conduit 44 may simply be an L-shaped passageway through which an integral combination pickup tube/drop tube is inserted or may be a passageway into the opposite ends of which separate pickup and drop tubes are inserted. The pickup and drop tubes 32 and 40 are preferably formed of a clear plastic or glass so that the blood sample collection operation can be closely monitored.

A vacuum tube 46 extends vertically through plug 22, the lower end in the preferred embodiment opening through the underside of plug portion 24 as shown best in FIG. 4. A tubular insert 48 protrudes upwardly from the top of the plug for engagement by the inlet spout 50 of a hand-held vacuum source 52. Any type of detachable connection between the hand-held vacuum source and vacuum tube 46 may be provided.

A main filter 54 is provided in the illustrated embodiment in the form of an annular ring in sealing engagement against the underside of plug 22 and having a center opening 56 to accommodate passage of the drop tube 40 therethrough. Filter $4 is preferably made of plastic or other material impervious to fluid flow through the filter. Rather, the exterior surface 58 is roughened to effectively form a plurality of grooves 60 which enable airflow between the filter 54 and interior periphery 62 of collection tube 12. The exterior diameter of filter 54 corresponds to the interior diameter of collection tube 12 so that air passing between the main filter 54 and collection tube is confined to the grooves 60.

Figure 2:
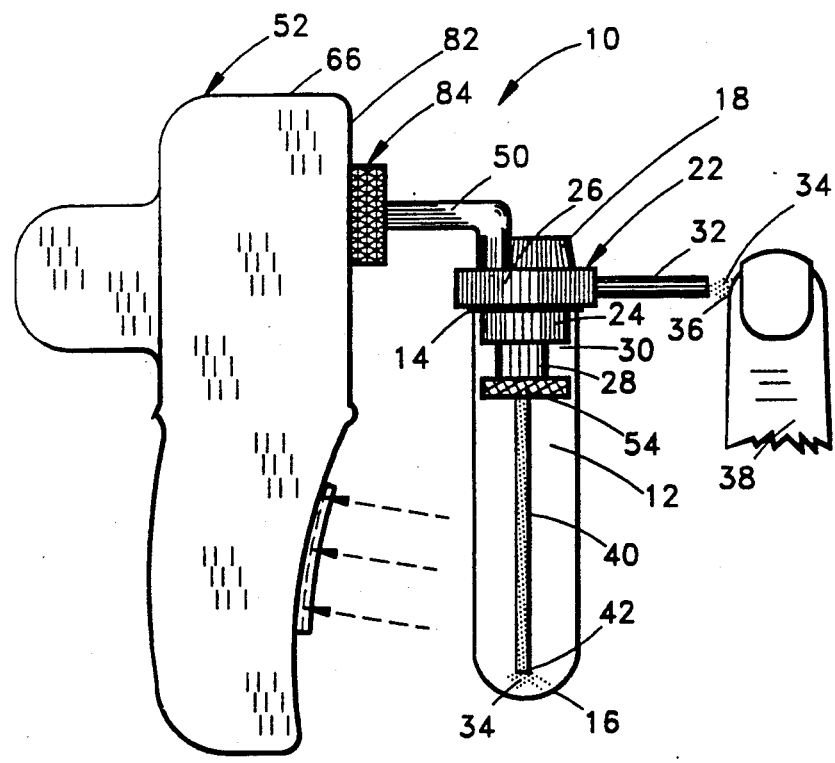
FIG. 2 is a side elevational view of the invention in use.
Figure 3:
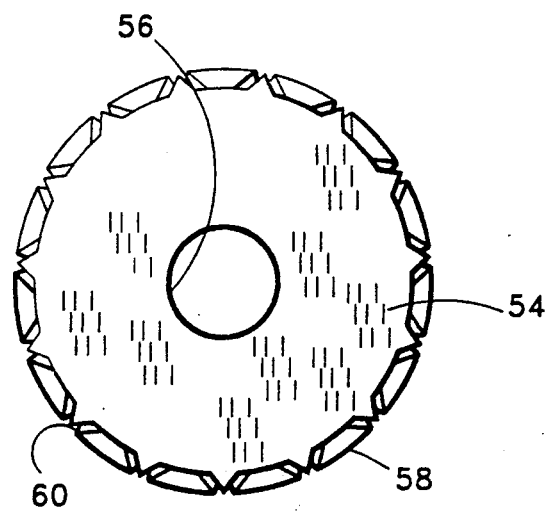
FIG. 3 is an enlarged top plan view of the main filter ring of the invention.

Referring to FIGS. 1 and 2, the pattern of grooves 60 may be crisscrossed as in a knurling pattern. The individual grooves may be arcuate or otherwise shaped so long as they are interconnected and extend from the upper edge to the lower edge of the main filter to enable the passage of air upwardly through the grooves between the main filter and collection tube wall. The main filter as thus formed provides an inexpensive yet effective device for preventing blood from being drawn into the vacuum source 52. This filter is operative regardless of the angle at which the tube is held and regardless of the extent to which the tube is filled within the capacity of the tube. Whereas main filter 54 may be adhered to the underside of plug 22, it is preferably held in place by frictional retention on drop tube 40.

Vacuum is provided from a portable hand-held vacuum sources 64 which includes a housing 66 which contains an electric vacuum pump 68 electrically connected to a pair of batteries 70 through an exteriorly accessible trigger switch 72.

Vacuum pump 68 has an inlet 74 connected by conduit 76 to an inlet port 78 embodied in a filter receptacle so on housing front wall 82. A conventional fiber disc filter is placed within the receptacle which is threaded for receiving a male threaded retainer 84 for spout 50. A circular fiber disc filter 86 prevents air born viruses from being spread in the ambient air exhausted by the vacuum pump 68 and also provides a last chance to prevent any blood in the air stream from being aspirated into the vacuum pump 68.

In operation, the blood collection tube 12 is provided with the plug 22, pickup tube 32, drop tube 40 and main filter 54 preassembled for connection as a unit to the vacuum source 64. Furthermore, an anticoagulant may be provided in the bottom of the tube either in the form of a liquid or a coating on the inside of the tube. The spout 50 of the vacuum source is connected to the tubular insert 48 of the vacuum tube 46 as shown in FIG. 4. The patient's finger, ear, or other body part is then pricked to present a droplet of blood. Trigger switch 72 of the vacuum source is depressed to apply a vacuum to the collection tube 12. The pickup tube 32 is moved into engagement with blood droplet to draw blood by the force of the vacuum through the pickup tube 32 and drop tube 40 for deposit at the base of the collection tube 12 in contact with the anticoagulant. The airflow through the tubes bubbles the blood and enhances mixing with the additive. The long length of the drop tube prevents the blood from sticking to the side of the collection tube above the anticoagulant and forming clots. Whereas the actual spacing of the bottom of the drop tube from the bottom surface of the collection tube is not critical to the invention, it is preferred that spacing be less than a diameter of the collection tube. Accordingly, blood from the drop tube will be directed into contact with the anticoagulant regardless of the angle at which the collection tube is held. This is important because it is not practical to require that the collection tube be vertically disposed in use. The way a patient holds his or her hand may dictate the best angle for the pickup tube to collect the blood so as to prevent blood from running down the finger, causing, a mess and possibly exposing the medical attendant to A.I.D.S. Likewise, there is often not enough room for pediatric nurses to hold the collection tube upright when collecting blood from a puncture site on an infant's heel due to positioning in a crib or for other reasons.

Once the blood sample has been collected in the tube 12 plug 22 is removed and disposed of whereupon the hinged cap 18 is inserted onto the open end of the tube. Cap 18 prevents spillage of the blood during handling of the tube and in the centrifuge. The cap minimizes air contact with the blood and resulting contamination. Since the cap is integral with the tube it won't get lost or misplaced.

In one embodiment, a vacuum pump 68 capable of generating a 12 millimeter mercury capacity vacuum was sufficient for the blood sample collection apparatus to operate effectively. A vacuum force of up to 3 psi or intermittent 8.5 psi is believed to be acceptable.

Thus there has been shown and described a blood sample collection apparatus which accomplishes at least all of the stated objects.

We claim:

1. A blood collection apparatus, comprising a blood collection tube having open and closed ends, a plug adapted to fit within and seal the open end of the blood collection tube, a vacuum tube extended through said plug for evacuating air from the blood collection tube, said vacuum tube having a lower end, a pickup tube protruding outwardly from said plug for drawing blood from a puncture site, a drop tube extending downwardly from said plug and having a lower end positioned within the blood collection tube and spaced substantially below the lower end of the vacuum tube, conduit means within said plug for connecting said pickup tube and drop tube so that blood drawn into said pickup tube is deposited into the blood collection tube through the lower end of the drop tube, a first filter on said plug and operatively interposed between the lower end of the vacuum tube and the air within said blood collection tube, said first filter being operative to allow gas flow therethrough but to block liquid flow therethrough, thus filtering the air drawn through said vacuum tube, a portable hand-held vacuum source including an inlet port and means for connecting said inlet port to said vacuum tube;

said first filter comprising a ring having an exterior surface engaging the interior periphery of the blood collection tube of the same diameter, said exterior surface having a plurality of grooves formed therein and extending from an upper edge to a lower edge thereof for filtering air directed through those grooves between said ring and interior periphery, the material of said ring being impervious to fluid flow therethrough but for through said exterior grooves, and the exterior diameter of said ring corresponding to the interior diameter of said blood collection tube such that air passing between said ring and blood collection tube is confined to said grooves.

2. The blood collection apparatus of claim 1 wherein said grooves comprise knurling on the exterior surface of said ring.

3. The blood collection apparatus of claim 1 wherein said ring has a center opening adapted to receive and be substantially filled by said drop tube.

4. The blood collection apparatus of claim 3 wherein said plug includes a stop shoulder situated in spaced relation below the lower end of the vacuum tube, said ring being engaged against said stop shoulder to partially define an airspace in said blood collection tube between said ring and vacuum tube.

5. The blood collection apparatus of claim 1 wherein said portable hand-held vacuum source comprises a housing, a vacuum pump mounted within said housing and operative to draw air through said inlet port and means for detachably connecting said inlet port to said vacuum tube.

6. The blood collection apparatus of claim 5 wherein said hand-held vacuum source includes a second filter operative to further filter air drawn into said inlet port.

7. The blood collection apparatus of claim 6 wherein said second filter comprises a disc filter.

8. The blood collection apparatus of claim 5 wherein said vacuum pump comprises an electric motor, means for supporting battery means within said housing and circuitry for connecting said electric motor to battery means at times.

9. The apparatus of claim 8 wherein said circuitry comprises an externally accessible trigger switch for actuating said vacuum pump.

* * * * *